(12) United States Patent
Raudaschl et al.

(10) Patent No.: US 12,188,823 B2
(45) Date of Patent: Jan. 7, 2025

(54) METHOD FOR DETERMINING A TOOTH COLOUR

(71) Applicant: Ivoclar Vivadent AG, Schaan (LI)

(72) Inventors: Patrik Raudaschl, Dornbirn (AT); Alen Frey, Nenzingen (AT)

(73) Assignee: Ivoclar Vivadent AG, Schaan (LI)

( * ) Notice: Subject to any disclaimer, the term of this patent is extended or adjusted under 35 U.S.C. 154(b) by 360 days.

(21) Appl. No.: 17/674,463

(22) Filed: Feb. 17, 2022

(65) Prior Publication Data
US 2022/0260420 A1  Aug. 18, 2022

(30) Foreign Application Priority Data

Feb. 18, 2021 (EP) .................................. 21158015

(51) Int. Cl.
| | |
|---|---|
| *G01J 3/50* | (2006.01) |
| *G01J 3/46* | (2006.01) |
| *G01J 3/52* | (2006.01) |
| *G06T 7/00* | (2017.01) |
| *G06T 7/11* | (2017.01) |

(Continued)

(52) U.S. Cl.
CPC ............... *G01J 3/508* (2013.01); *G01J 3/463* (2013.01); *G01J 3/52* (2013.01); *G06T 7/0014* (2013.01); *G06T 7/11* (2017.01); *G06T 7/30* (2017.01); *G06T 7/60* (2013.01); *G06T 7/90* (2017.01); *G06T 2207/10024* (2013.01); *G06T 2207/20021* (2013.01); *G06T 2207/20081* (2013.01); *G06T 2207/20084* (2013.01); *G06T 2207/30036* (2013.01)

(58) Field of Classification Search
CPC .. G01J 3/508; G01J 3/463; G06T 7/11; G06T 7/30; G06T 7/90; G06T 7/0014; G06T 7/60
See application file for complete search history.

(56) References Cited

U.S. PATENT DOCUMENTS

| | | |
|---|---|---|
| 9,008,417 B2 | 4/2015 | Rohner et al. |
| 9,662,188 B2 | 5/2017 | Laubersheimer et al. |
| (Continued) | | |

FOREIGN PATENT DOCUMENTS

| | | |
|---|---|---|
| EP | 3613381 A1 | 2/2020 |
| WO | 0063661 A1 | 10/2000 |

*Primary Examiner* — Kevin Ky
(74) *Attorney, Agent, or Firm* — Ann M. Knab; Thad McMurray

(57) ABSTRACT

A method for determining a tooth colour providing an evaluation device having an iterative learning algorithm using CNNs which captures and evaluates images under different light conditions and capture angles and learns the assignment to the applicable pattern tooth colour. In an evaluation step, a capture device is provided with which an image of an auxiliary body with a previously known pattern tooth colour is captured together with at least one tooth. The capture device acquires at least two images of the combination of the tooth to be determined and the auxiliary body from different capture angles and forwards them to the evaluation device. The evaluation device, based on the assignment learned to the applicable sample tooth colour, evaluates the captured images and outputs the tooth colour of the tooth to be determined according to a reference value, such as a common tooth key, e.g. A1, B2, etc.

21 Claims, 4 Drawing Sheets

(51) Int. Cl.
*G06T 7/30* (2017.01)
*G06T 7/60* (2017.01)
*G06T 7/90* (2017.01)

(56) References Cited

U.S. PATENT DOCUMENTS

| | | | |
|---|---|---|---|
| 9,934,188 B2 | 4/2018 | Chiba | |
| 10,007,987 B1 | 6/2018 | Braunston | |
| 10,510,000 B1 | 12/2019 | Commons | |
| 10,543,067 B2 | 1/2020 | Tanaka | |
| 11,030,746 B2* | 6/2021 | Wang | G16H 20/40 |
| 11,087,470 B2 | 8/2021 | Mehnert et al. | |
| 11,093,800 B2 | 8/2021 | Tang | |
| 11,094,085 B2 | 8/2021 | Lerch et al. | |
| 11,138,437 B2 | 10/2021 | Cho et al. | |
| 11,176,404 B2 | 11/2021 | Zhao et al. | |
| 11,195,265 B2 | 12/2021 | Kim | |
| 11,216,693 B2 | 1/2022 | Krueger et al. | |
| 11,222,256 B2 | 1/2022 | Teng et al. | |
| 11,244,195 B2 | 2/2022 | Pao et al. | |
| 11,250,580 B2 | 2/2022 | Meyer et al. | |
| 2004/0078299 A1* | 4/2004 | Down-Logan | G06Q 30/02 705/26.1 |
| 2013/0244197 A1* | 9/2013 | Tjioe | G01J 3/0264 433/29 |
| 2018/0168781 A1* | 6/2018 | Kopelman | A61B 34/10 |
| 2018/0174367 A1* | 6/2018 | Marom | G06T 19/006 |
| 2019/0350680 A1* | 11/2019 | Chekh | G06T 15/83 |
| 2020/0060798 A1 | 2/2020 | Lerch et al. | |
| 2021/0140763 A1* | 5/2021 | Pesach | A61B 1/0605 |
| 2022/0122231 A1* | 4/2022 | Gupta | G06V 10/56 |
| 2022/0168074 A1* | 6/2022 | Bogdanic | A61C 9/0053 |
| 2022/0168079 A1* | 6/2022 | Dang | A61C 13/082 |
| 2022/0260420 A1* | 8/2022 | Raudaschl | G06T 7/60 |
| 2023/0039451 A1* | 2/2023 | Lee | G16H 40/20 |
| 2023/0149129 A1* | 5/2023 | Oren-Artzi | A61C 7/002 |
| 2023/0334549 A1* | 10/2023 | Pellissard | G06Q 30/0631 |

* cited by examiner

Fig. 4: algorithm as a function with input and output
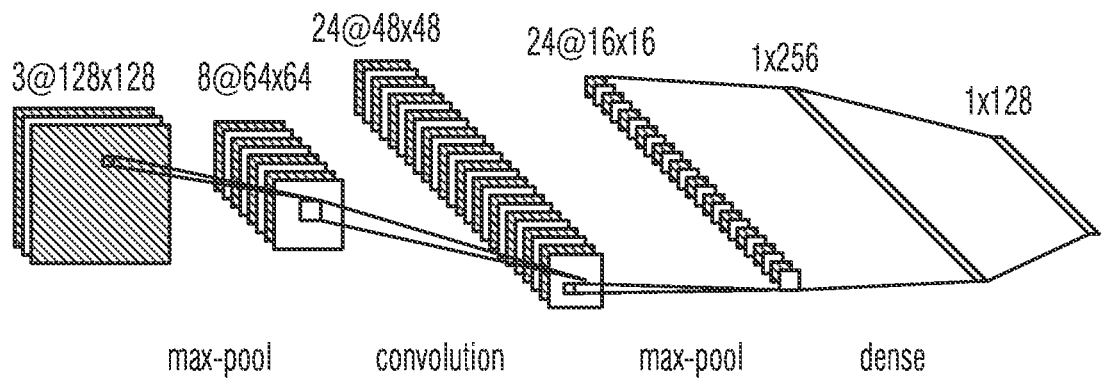
Fig. 5: schematic representation of a CNN
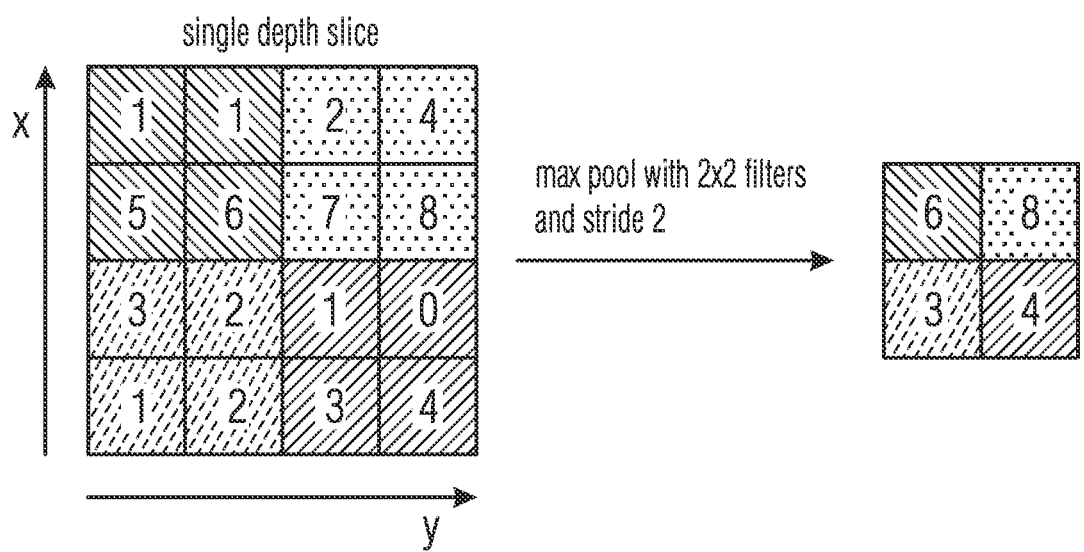
Fig. 6: max pooling layer

METHOD FOR DETERMINING A TOOTH COLOUR

CROSS-REFERENCE TO RELATED APPLICATIONS

This application claims priority to European patent application No. 21158015.4 filed on 5 Feb. 18, 2021, the disclosure of which is incorporated herein by reference in its entirety.

TECHNICAL FIELD

The invention relates to a method for determining a tooth colour.

BACKGROUND

From EP 3 613 382 A1 and corresponding US 20200060798, which US published application is hereby incorporated by reference in its entirety, the use of a colour selection body which is held next to a tooth whose tooth colour is to be determined, first became known. A common image of the tooth and the colour selection body formed as an auxiliary body is taken. Since the auxiliary body has a known tooth colour, this makes it easier and more accurate to determine the colour of the tooth.

The solution mentioned above requires reproducible lighting conditions if possible. While the presence of the auxiliary body with the known tooth colour allows the colour of the tooth to be calibrated or standardised, it has been shown that despite this possibility, deviations occur in practice, such that the accuracy of the colour determination that can be realised in the laboratory does not exist in practice.

U.S. Pat. Nos. 11,094,085, 10,543,067, 10,007,987, 9,934,188, 9,662,188, 9,008,417, 9,662,188, are directed to dental materials and/or colour methods and devices for dental materials and are hereby incorporated by reference in their entirety.

SUMMARY

The invention is based on the task of creating a method for determining a tooth colour that also ensures accurate colour determinations in practice.

This task is solved according to the invention by the independent claim(s). Advantageous further embodiments result from the sub-claims.

According to the invention, it is provided that an evaluation device first acquires and evaluates images of sample teeth in an iterative learning algorithm under different lighting conditions and acquisition angles and learns an assignment of the images acquired to the known applicable sample tooth colour.

In particular, the acquisition and learning at different acquisition angles is important according to the invention and contributes significantly to improving the recognition capability of the evaluation device.

An initial acquisition device is used to acquire images of sample teeth. This initial capture device can be of particularly high quality. Examples include, but are not limited to, a professional SLR camera, the raw data of which can be read out. The quality of the raw data is typically better than that of the camera data converted into a standard format such as JPG.

Other examples include, but are not limited to a camera of a terminal device as the initial capture device, for example that of a smartphone. Other types of acquisition devices known to one of ordinary skill in the art are also useful herein.

A capture device, for example another capture device, is used in an evaluation step. In the evaluating step, an image of a tooth whose colour is to be determined is taken together with the auxiliary body having the known colour.

The evaluation device accesses the learned images and the image data acquired with them.

The evaluation device preferably has a first part which is used in the preparatory step and a second part which is used in practice in the evaluation device, although the invention is not limited to a single device with two parts, and therefore two different devices may be used for the preparatory step and the evaluation step.

The second part accesses the same data as the first part.

This makes it possible to use the evaluation device on site, for example in a dental practice, without having to do without the data obtained in the preparatory step.

In order to enable easy access to the data and findings obtained, it is preferable that these are stored in a cloud or at least in an area that is protected on the one hand and accessible in practice on the other.

In practice, the second part of the evaluation device is then used, which accesses the same data as the first part.

These data are therefore always available to the evaluation device. However, this does not mean that full access to the data is required at all times in the method according to the invention.

Rather, it is preferred that the evaluation device has a memory in the second part, the contents of which are periodically synchronised with the cloud.

What the second part of the evaluation device then does is an evaluation of the images captured by the further capture device and an assignment of these to sample tooth colours, based on the learned assignment to sample tooth colours, and then the output of the tooth colour according to a common tooth key based in turn thereon.

In this case, the sample tooth colour does not have to be real and stored; a virtual generation of the sample tooth colour, i.e. the definition in a defined colour space, is sufficient. It is also possible to generate a tooth colour only numerically in a virtual colour space, preferably in RGB space, and to use this as a reference. Such a colour is referred to here as an RGB tooth colour, whereby it is understood that this also includes colours generated in other virtual tooth spaces.

There are several ways to create such a virtual tooth colour:

1. using a scan of a tooth and the determination of the corresponding RGB values;
2. using the values of existing tooth libraries; or
3. using colour measuring devices such as photospectrometers to determine the colours numerically.

Surprisingly, the variety of imaging situations in the preparatory step results in much better recognition and determination of the actual colour of the tooth to be determined.

Imaging situations include those where different light sources and brightnesses are used.

For example, the same sample teeth can be photographed with the light spectrum of a halogen lamp, an LED lamp and daylight in sunshine and, on the other hand, under a cloudy sky. Moreover, this can be done at three different brightness levels. And also at 5 to 15 different imaging angles in vertical and horizontal directions.

These preparations lead to a profound data base of, for example, but not limited to, 100 to 300 different imaging situations for each sample tooth.

It is understood that the above explanation is merely exemplary and, in particular, that the invention is not limited to the number of imaging situations in the preparatory step.

In an advantageous embodiment of the method according to the invention, it is provided to check in the preparatory step at the iteration to what extent the result changes in each iteration. If the result changes less than a predetermined threshold value, it is assumed that the desired accuracy has been achieved.

This design can also be modified so that the iteration is only terminated after the change has fallen below the threshold value several times.

Preferably, after completion of the preparatory step, it is ensured that all determined data, which comprise the association between the result of the preparatory step and the sample tooth shades, are transferred to a cloud where they can be accessed if necessary.

Before an evaluation step is performed by a terminal, it performs a data synchronisation in such a way that the determined data are stored locally on the terminal as far as necessary and in particular completely.

This data is synchronised regularly so that changes reach the terminals regularly.

When the terminal device is to carry out the evaluation step, the current data of the evaluation device, as far as they were provided and made available in the preparatory step, are therefore always available.

The first part of the evaluation device is exclusively active in the preparatory step, but is still available if further lighting conditions or capture angles are to be captured.

In the event that the lighting conditions and exposure angles relevant in practice have been captured, but detailed adjustments may still be useful, the evaluation device can also be transferred to the cloud as an executable or compilable program.

This solution has the advantage that a dentist can also use the evaluation device in its first part himself if he has the necessary equipment and can even take into account his particular lighting conditions, provided that he has sample tooth shades available which he needs to carry out the first step.

The dentist can then make the data he has determined in this way and which is new with regard to the special lighting conditions available to other dentists in the cloud, if desired.

Similar handling is also possible if a region-specific adjustment is desired:

The light spectrum of daylight differs geographically between regions close to the equator and regions close to the poles, as the absorption bands of the air envelope have a much stronger effect in regions close to the poles.

If an average value of the daylight is used as a basis in the first step, it is possible that a dentist in a region close to the equator will come to the conclusion, based on the data provided by the evaluation device, that the set daylight data require a correction.

He can then make the regionally adjusted data available to other dentists in his area, for example in the cloud.

This is only one example of the preferred possibilities according to the invention for enabling data exchange of the provided data in the cloud. It is understood that data exchange for other reasons is also encompassed according to the invention.

For the actual evaluation in the evaluation device, it is convenient if reference points are provided on the auxiliary body. The reference points are selected in such a way that they can be recognised by the evaluation device. If, for example, three or four reference points are provided, the angle at which the image was captured can be deduced from their arrangement in the captured image.

According to the invention, it is advantageous if a conclusion or a comparison with the data associated with the relevant angle of capture is made from this angle detection.

In a further advantageous embodiment, a division of the captured image into segments is provided.

The segmentation has the advantage that areas can be masked out whose data acquired in the evaluation step indicate the presence of reflections.

Surprisingly, this measure can significantly increase the precision of the evaluations, especially in bright and thus reflection-prone environments.

Various parameters can be used for the evaluation carried out by the evaluation device:

For example, it is possible to carry out a normalisation to the brightness of the environment by means of an ambient light sensor. Typically, end devices such as smartphones have an ambient light sensor that typically adjusts the brightness of the display.

In an advantageous embodiment of the invention, this ambient light sensor is utilised to perform the aforementioned normalisation.

High-quality smartphones can also differentiate spectrally between artificial light and daylight. This distinction is also made by the built-in ambient light sensor. According to the invention, this differentiation result can also be exploited preferentially by not making the non-applicable data available to the evaluation device from the outset.

It is preferable that the method for determining a tooth colour includes providing an evaluation device having an iterative learning algorithm using CNNs, in a preparatory step, based on at least one previously known sample tooth colour, preferably wherein the previously known sample tooth colour is generated virtually in RGB space, the evaluation device acquires and evaluates images under different lighting conditions and capture angles and learns to assign the images to the applicable sample tooth colour, in an evaluation step, a capture device is provided, the capture device captures an image of an auxiliary body with a previously known pattern tooth colour together with at least one tooth, the capture device acquires at least two images of the combination of the at least one tooth to be determined and the auxiliary body from different capture angles and feeds the at least two images to the evaluation device, and the evaluation device, based on the learned assignment to the applicable sample tooth colour, evaluates the captured images and outputs the tooth colour of the tooth to be determined according to a reference value.

It is preferable that the capture device includes a camera of a terminal device, such as a smartphone, or a scanner is provided, that the previously known pattern tooth colour is virtually generated, and that the reference value includes a common tooth key, e.g. A1, B2, etc.

It is preferable that, in the preparatory step, iteration of the learning algorithm is terminated when accuracy of the assignment to the applicable sample tooth colour exceeds a threshold value, or a change of data provided in the iteration with respect to data of a previous iteration falls below a threshold value.

It is preferable that, at the end of the preparatory step, the evaluation device or data from the evaluation device is or are transferred to a cloud, and, in the evaluation step, the transfer of the at least two images to the cloud occurs.

It is preferable that the terminal device outputs the tooth colour of the tooth to be determined.

It is preferable that the auxiliary body has reference points and, in the evaluation step, the evaluation starts only if the reference points are detected in the image to be evaluated and, another image is requested if no reference points are detected.

It is preferable that, in the evaluation step, the evaluation device divides the image to be evaluated into segments, after detecting reference points.

It is preferable that, in the evaluation step, the evaluation device determines a segment from among the segments to be a tooth segment if the segment has a surface in a shape of a tooth or shape of a tooth-part and with tooth-like minor differences in colour and brightness.

It is preferable that, in the evaluation step, the evaluation device defines one of the segments as an auxiliary body segment.

It is preferable that, in the evaluation step, the evaluation device searches for reflections in the tooth segment and/or the auxiliary body segment, and only continues the evaluation if only reflections below a predetermined threshold value are detected, and requests another image if the reflections exceed the predetermined threshold value.

It is preferable that, in the evaluation step, the evaluation device determines dominant colours of the tooth segment, and carries out the evaluation based on the assignment learned, taking into account different lighting conditions, according to a method of the smallest colour distance.

It is preferable that, in the evaluation step, the evaluation device also carries out the evaluation based on a comparison of the colour and brightness values of the auxiliary body segment or segments and of the tooth segment.

It is preferable that the capture device includes an ambient light sensor, the output signal of which is fed to the evaluation device.

It is preferable that the evaluation device, after a predetermined number of evaluations, carries out the preparatory step again, taking into account any evaluations that have been carried out.

It is preferable that the evaluation device has a geometry detection unit which emits a warning signal based on an alignment or non-parallelism of segment boundaries, and that the evaluation device displays the warning signal as an indication of a desired alignment of the terminal device to be changed on the screen thereof.

It is preferable that known tooth shapes occurring in practice for defining the segments and/or for improving the geometry detection are stored in the evaluation device and are compared with the detected shapes or segment boundaries.

It is preferable that the capture device is designed as a camera and the evaluation device comprises a smartphone app, said app performing at least part of the evaluation via the evaluation device.

It is preferable that the capture device is designed as a scanner, where said scanner integrates a computer, in particular a mini-computer such as a Raspberry Pi, which performs at least part of the evaluation via the evaluation device.

It is preferable that the method for determining a tooth colour, includes providing an evaluation device having an iterative learning algorithm using CNNs, in a preparatory step, based on at least one previously known RGB tooth colour, the evaluation device acquires and evaluates images under different lighting conditions and capture angles and learns to assign the images to the applicable RGB tooth colour, in an evaluation step, a capture device is provided, the capture device may include a camera of a terminal device, such as a smartphone, or a scanner, the capture device captures an image of an auxiliary body with a previously known RGB tooth colour together with at least one tooth, the capture device captures at least two images of the combination of the tooth to be determined and the auxiliary body from different capture angles and feeds them to the evaluation device, and the evaluation device, based on the learned assignment to the applicable RGB tooth colour, evaluates the acquired images and outputs the tooth colour of the tooth to be determined according to a reference value, such as a common tooth key, e.g. A1, B2, etc.

It is preferable that a computer program product for a method for determining a tooth colour is provided having program code which is stored on a non-transitory machine-readable medium, the machine readable medium comprising computer instructions executable by a processor, which computer instructions cause an evaluation device to perform the method for determining a tooth colour described herein.

BRIEF DESCRIPTION OF THE DRAWINGS

Further advantages, details and features will be apparent from the following description of an embodiment of the method according to the invention with reference to the drawings, wherein:

FIG. 4 shows a learning algorithm according to the invention as a function with input and output;

FIG. 5 shows a schematic representation of a CNN convolution layer in the algorithm; and FIG. 6 shows a schematic representation of an example of max pooling.

DETAILED DESCRIPTION

Figure 1:
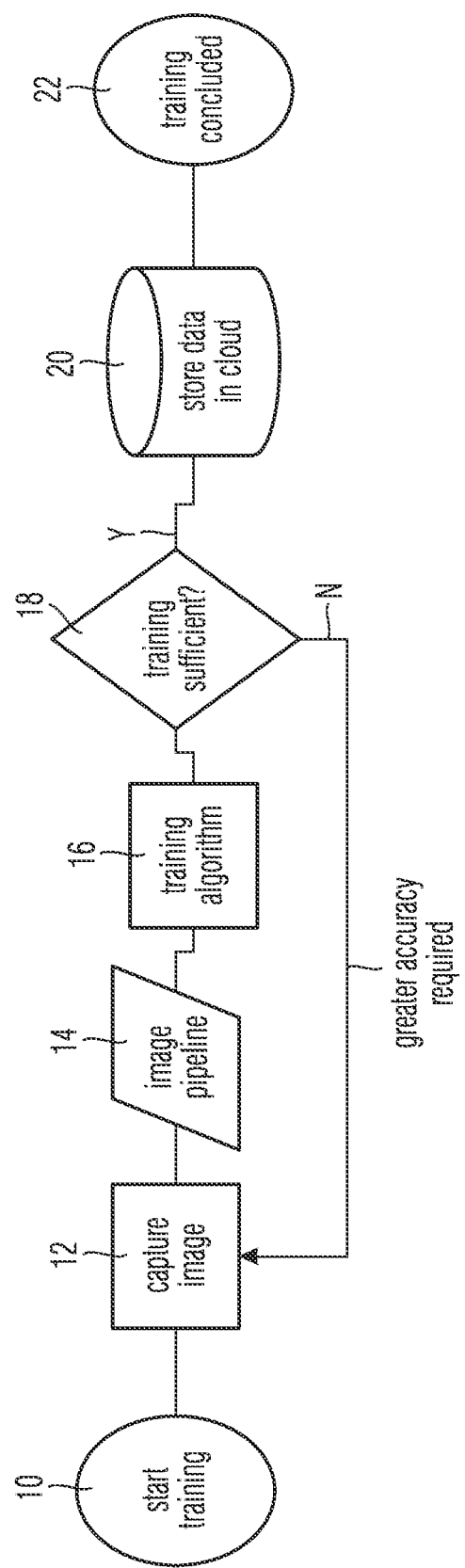
FIG. 1 shows a schematic flow diagram of the preparatory step according to the invention.

FIG. 1 schematically illustrates the preparatory step 12 of the method of the invention for determining a tooth colour. The preparatory step 12 is referred to here as training 10 and, according to the flowchart of FIG. 1, begins with the start of the training 10.

First, images, which can also be referred to as "captures", are captured in step 12. The captures represent sample tooth colours and the corresponding teeth formed as samples are captured, acquired and evaluated under different lighting conditions and at different angles of capture.

Figure 2:
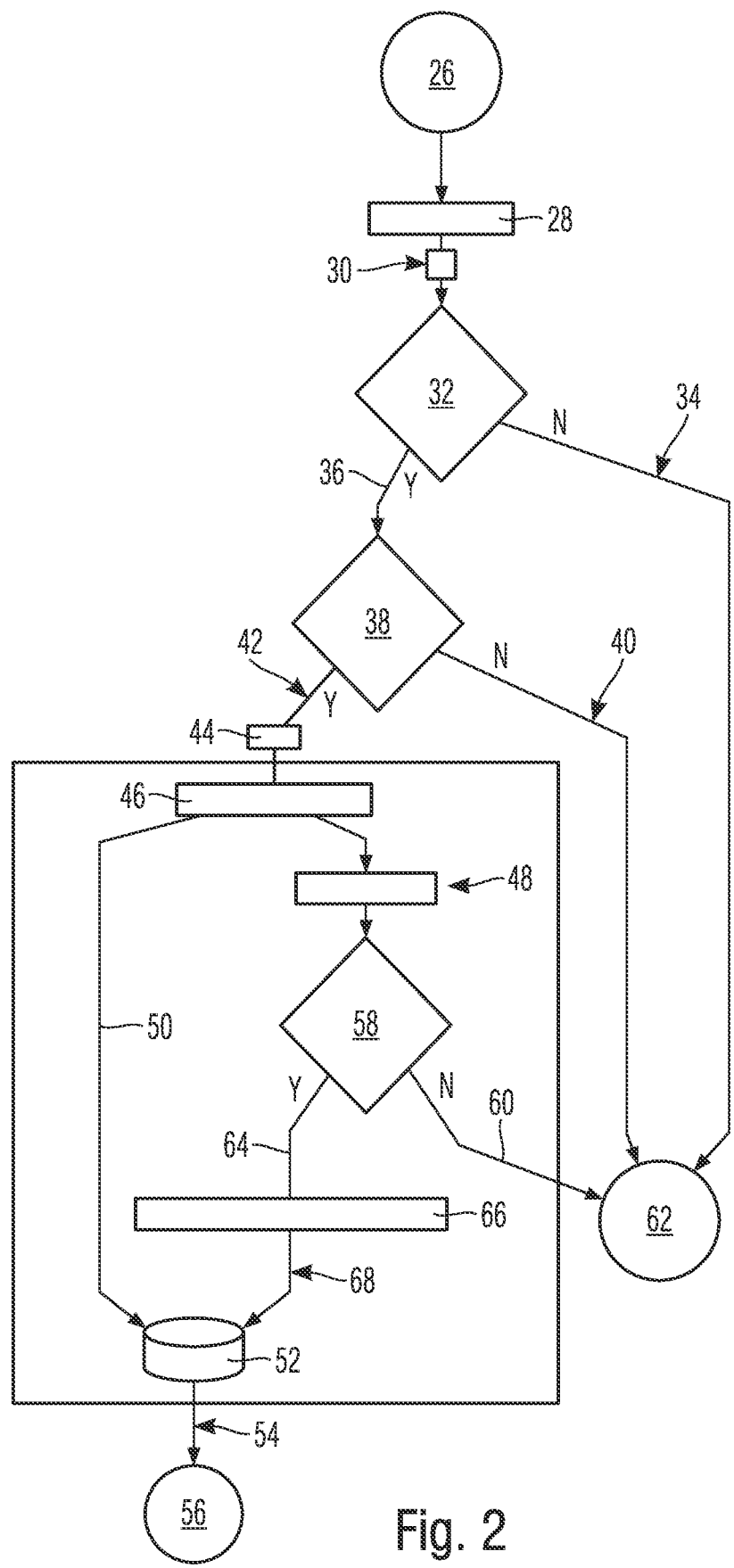
FIG. 2 shows a schematic flow chart of the image pipeline as a subroutine used in both the preparatory step and the evaluation step.

The captured data is fed to an image pipeline 14 as a subroutine, the design of which can be seen in FIG. 2.

After processing in the image pipeline 14, the processed data is forwarded to a training algorithm 16. This algorithm carries out the actual training, i.e. the optimised reproduction of the sample tooth colours under the different lighting conditions and capture angles of the form of data.

Subsequently, in step 18, a check is made as to whether the training was sufficient. If this has not been the case, i.e. greater accuracy is required, a return is made to block 12 and the acquired data passes through the image pipeline 14 again.

If, on the other hand, the training is deemed sufficient, the "trained" data is stored in the cloud, at step 20. This concludes the training at block 22.

FIG. 2 shows the individual steps of the image pipeline 14. The image pipeline 14 is started in step 26. Image data 28 is available, which is stored in the image memory in step 28.

The image 30 is now available and its resolution and format are checked in step 32. If the resolution and format are insufficient, path 34 is taken, while if both format and resolution are sufficient, execution continues with path 36.

The image 30 is checked in path 36 to see, in step 38, where the reference points of the reference object are; these are acquired. Again, the possibility arises in path 40 that no or insufficient reference points were able to be determined.

If, on the other hand, reference points were able to be found, path 42 is continued and the relevant information is extracted from the image 30 in block 44. This includes colour values extracted from the reference object according to block 46.

A check is made to see if a tooth segment exists in image 30. If this is the case, path 48 is taken.

In parallel, colour values are processed with path 50. The colour values are forwarded to the algorithm at block 52, which uses them to generate the colour information of the image 30 in path 54, and the data transfer to the calling programme, i.e. the end of the sub-programme image pipeline, takes place in block 56.

According to path 48, the tooth segment data is also processed further. In block 58 a check is made to see if reflections are present. If these are above a threshold value, path 60 is taken, which, like path 34 and path 40, ends with no result according to block 62.

If, on the other hand, according to path 64 the reflections are below a set value, dominant tooth colours are calculated by so-called k-means clustering. This is done in block 66.

This results in colour values in path 68, which in turn are fed to algorithm 52.

Figure 3:
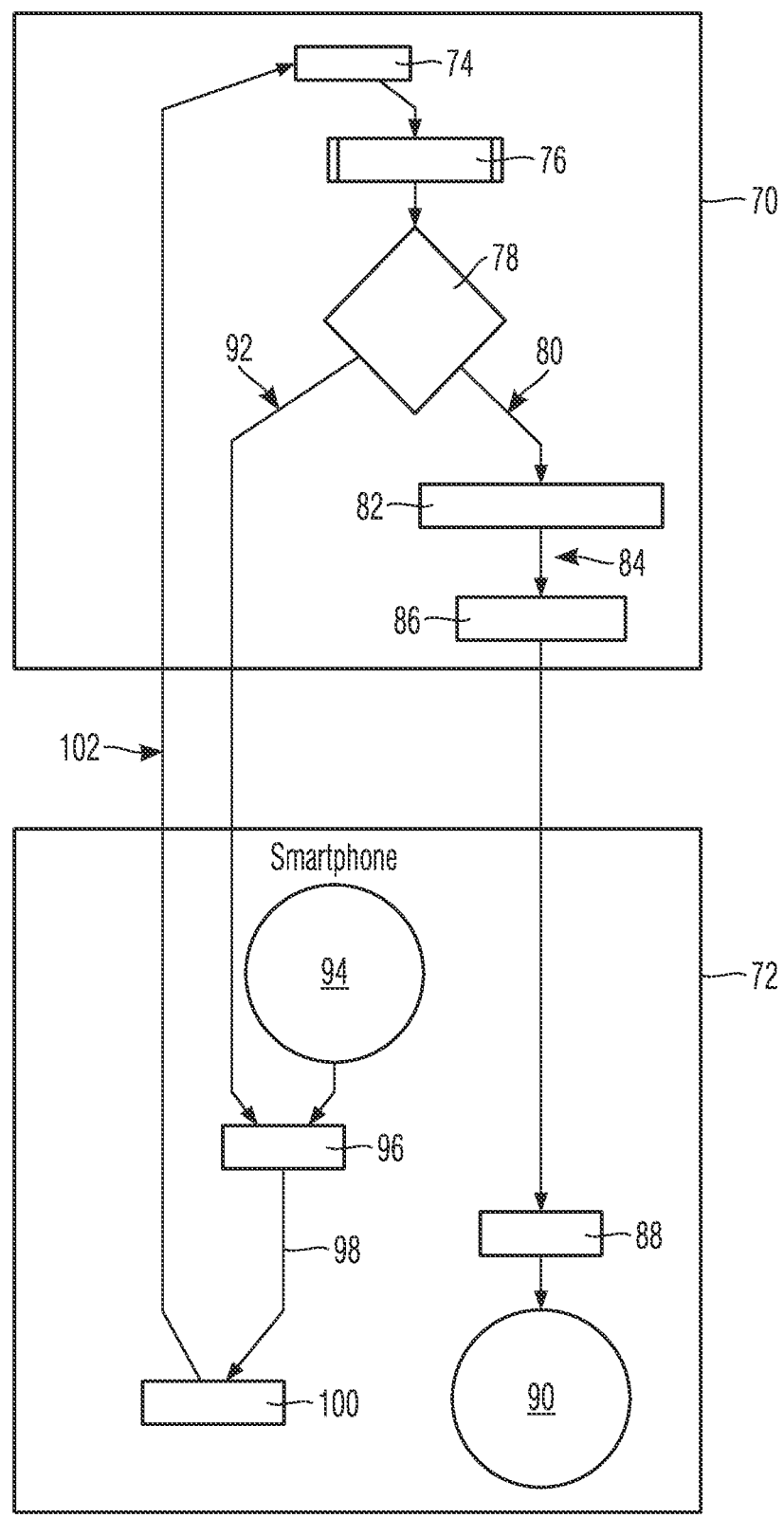
FIG. 3 shows a schematic flow diagram of the evaluation step.

FIG. 3 shows the evaluation step. This is intended to be executed in the end device, for example a smartphone. A first block 70 represents the cloud, and a second block 72 represents the smartphone.

In an advantageous embodiment, the data of the image captured by the end user is sent to the cloud in block 74, and it enters the image pipeline in block 76 (FIG. 2). This image pipeline is the same as the image pipeline 14 in FIG. 1.

After processing and evaluating the data, at step 78 a check is made to see if there are enough images. If this is the case, path 80 is taken and a classification algorithm is carried out in block 82. On the output side of block 82, classified colours are thus available at block 84. These are routed to the smartphone 72 via block 86.

The smartphone receives the data in block 88 and the colour classification is completed in block 90.

If, on the other hand, it is determined at step 78 that there are not enough images, path 92 is taken. In this case, colour classification is started by the smartphone in block 94 and a picture is taken at 96.

The taking of the picture or the image is thus triggered or initiated via path 92.

On the output side of the smartphone 72, there is an image in path 98. In block 100, this image is routed to the cloud via path 102 and loaded there so that execution in block 74 can start at this image.

An example learning algorithm is described below:

When the algorithm is fully trained, it can be seen, as shown in FIG. 4, at the highest level as a function that assigns to each input image a natural number (including 0) from 0 to N (number of classes). The output numbers represent the different classifications; thus, the upper limit of the numbers depends on the use case or the number of different objects to be classified. In the embodiment according to the invention, these are the 16 different colours of the tooth shade guide, (A1-D4) Examples of shade guides include but are not limited to the Vita Shade Guide, well known to one or ordinary skill in the art.

FIG. 4 shows the algorithm as a function with input and output. This algorithm belongs to a variation of neural networks, the so-called CNNs (convolutional neural networks). CNNs are neural networks that are primarily used to classify images (i.e. name what they see), group images by similarity (photo search) and recognise objects in scenes. For example, CNNs are used to identify faces, people, street signs, tumours, animals and many other aspects of visual data.

Experiments have shown that CNNs are particularly effective in image recognition and enable Deep Learning. The intrinsically well-known Deep Convolutional architecture called AlexNet (ImageNet competition 2012) can be used; at the time, applications thereof were addressed for self-driving cars, robotics, drones, security, medical diagnostics.

The CNNs of the invention, as used, do not perceive images as humans do. On the contrary, the decisive factor is how an image is fed to a CNN and processed by it.

On the contrary, CNNs perceive images as volumes, i.e. as three-dimensional objects, rather than as a flat canvas measured only by width and height. This is because digital colour images have a red-blue-green (RGB) coding, where these three colours are mixed to create the colour spectrum perceived by humans. A CNN takes such images as three separate layers of colour stacked on top of each other.

In this way, a CNN receives a normal colour image as a rectangular box whose width and height are measured by the number of pixels in these dimensions and whose depth comprises three layers, one for each letter in RGB. These depth layers are called channels.

These numbers are the initial, raw, sensory features that are fed into the CNN, and the purpose of the CNN is to find out which of these numbers are significant signals that help it to classify images more accurately according to particular classes.

CNNs roughly consist of three different layers through which input images are consecutively propagated via mathematical operations. The number, properties and arrangement of the layers can be changed according to the application purpose in order to optimise the results. FIG. 5 shows a possible CNN architecture. The following sections describe the different layers in more detail.

FIG. 5 shows a schematic representation of a CNN convolution layer. Instead of focusing on one pixel at a time, a CNN takes square regions of pixels and runs them through a filter. This filter is also a square matrix that is smaller than the image itself and the same size as the field. It is also called a kernel, and the filter's job is to find patterns in the pixels. This process is called folding or convolution.

An example visualisation of the folding can be seen in the following link: https://cs231n.github.io/assets/conv-demo/index.html. Examples of convolution or folding are found in U.S. Pat. Nos. 11,244,195, 11,222,256, 11,176,404, 11,138,437, 11,093,800 and 11,087,470, which are hereby incorporated by reference in their entirety.

The next layer in a CNN has three names: Max-Pooling, Downsampling and Subsampling. FIG. 6 shows an exemplary max pooling layer. Inputs from the previous layer are fed into a downsampling layer, and as with convolutions, this method is applied patchwise. In this case, max pooling simply takes the largest value from one field of an image (see FIG. 6), inserts it into a new matrix alongside max values from other fields, and discards the rest of the information contained in the activation maps.

A lot of information about lower values is lost in this step, which has stimulated research into alternative methods. However, downsampling has the advantage of reducing the amount of storage and processing required, precisely because information is lost.

Dense Layer

Dense layers are "traditional" layers that are also used in classical neural networks. They consist of a variable number of neurons. Neurons in such layers have complete connections to all outputs in the previous layer, as in normal neural networks. Their outputs can therefore be calculated with matrix multiplication followed by a bias offset. For further explanation, please refer to the following link in full: www.adventuresin-machinelearning.com/wp-content/uploads/2020/02/A-beginners-introduction-to-neural-networks-V2.pdf. U.S. Pat. Nos. 11,250,580, 11,195,265 and 11,216,693 are directed to using neural networks and are hereby incorporated by reference in their entirety.

Learning Process

The learning process of CNNs is largely identical to the process of classical neural networks. In this respect, full reference is made to the following link: https://futurism.com/how-do-artificial-neural-networks-learn. U.S. Pat. No. 11,216,693 and 10,510,000 are directed to artificial neural networks and are hereby incorporated by reference in their entirety.

While CNNs have so far been used exclusively for recognising objects in images, according to the invention this architecture is used to classify colours of objects with very high accuracy.

In some embodiments, a camera, processor, electronic data storage unit, and digital display are components of a single device. The single device may be a smartphone, tablet, laptop computer, personal digital assistant, or other computing device.

In some embodiments, the processor is in communication over a network, which could be wired or wireless, with an external processor used for performing one or more calculation steps and/or a network-attached electronic data storage unit. In some embodiments, the present disclosure makes use of cloud computing to perform one or more calculations steps remotely and/or remote storage to enable the storage of data remotely for collaborative or remote analysis. In some embodiments, the system comprises a plurality of graphical user interfaces to permit multiple users to view or analyze the same data.

Where used herein, the term "non-transitory" is a limitation on the computer-readable storage medium itself—that is, it is tangible and not a signal—as opposed to a limitation on the persistence of data storage. A non-transitory computer-readable storage medium does not necessarily store information permanently. Random access memory (which may be volatile, non-volatile, dynamic, static, etc.), read-only memory, flash memory, memory caches, or any other tangible, computer-readable storage medium, whether synchronous or asynchronous, embodies it.

Although the invention is illustrated above, partly with reference to some preferred embodiments, it must be understood that numerous modifications and combinations of different features of the embodiments can be made. All of these modifications lie within the scope of the appended claims.

The invention claimed is:

1. A method for determining a tooth colour, comprising
providing an evaluation device having an iterative learning algorithm using Convolutional Neural Networks (CNNs), wherein the algorithm is trained on previously known sample tooth colours,
in a preparatory step, based on previously known sample tooth colours, acquiring images of one or more tooth colours under different lighting conditions and different capture angles, where in the one or more tooth colours are perceived as three separate layers,
in an evaluation step, evaluating the images using the evaluation device and assigning the images of each of the one or more tooth colours to a sample tooth colour based on learned mapping from the known sample tooth colour, thereby creating a learned assignment for each sample tooth colour,
providing a capture device, which device captures an image of an auxiliary body having a previously known tooth colour together with at least one tooth with an undetermined colour,
acquiring, using the capture device, at least two images of the combination of the at least one tooth with an undetermined colour and the auxiliary body from different capture angles and feeding the at least two acquired images to the evaluation device, and
evaluating, using the evaluation device, the at least two acquired images, and outputting, based on the learned assignment to each of the sample tooth colours, a calculated tooth colour for the tooth with the undetermined colour according to a reference value, which comprises a tooth colour key.

2. The method according to claim 1,
wherein the previously known sample tooth colour is generated virtually in RGB space,
wherein the capture device comprises a camera of a terminal device,
wherein the previously known pattern tooth colour is virtually generated.

3. The method according to claim 2,
wherein the terminal device outputs the tooth colour of the tooth with the undetermined colour.

4. The method according to claim 1,
wherein, in the preparatory step, iteration of the learning algorithm is terminated when accuracy of the assignment to the applicable sample tooth colour exceeds a threshold value, or a change of data provided in the iteration with respect to data of a previous iteration falls below a threshold value.

5. The method according to claim 1,
wherein, at the end of the preparatory step, the evaluation device or data from the evaluation device is or are transferred to a cloud, and, in the evaluation step, the transfer of the at least two images to the cloud occurs.

6. The method according to claim 1,
wherein the auxiliary body has reference points and, in the evaluation step, the evaluation starts only if the reference points are detected in the image to be evaluated and, another image is requested if no reference points are detected.

7. The method according to claim 1,
wherein, in the evaluation step, the evaluation device divides the image to be evaluated into segments, after detecting reference points.

8. The method according to claim 7,
wherein, in the evaluation step, the evaluation device determines a segment from among the segments to be a tooth segment if the segment has a surface in a shape of a tooth or shape of a tooth-part and with tooth-like minor differences in colour and brightness.

9. The method according to claim 8,
wherein, in the evaluation step, the evaluation device defines one of the segments as an auxiliary body segment.

10. The method according to claim 9,
wherein, in the evaluation step, the evaluation device searches for reflections in the tooth segment and/or the auxiliary body segment, and only continues the evaluation if only reflections below a predetermined threshold value are detected, and requests another image if the reflections exceed the predetermined threshold value.

11. The method according to claim 9,
wherein, in the evaluation step, the evaluation device also carries out the evaluation based on a comparison of the colour and brightness values of the auxiliary body segment or segments and of the tooth segment.

12. The method according to claim 8,
wherein, in the evaluation step, the evaluation device determines dominant colours of the tooth segment, and carries out the evaluation based on the assignment learned, taking into account different lighting conditions.

13. The method according to claim 7,
wherein the evaluation device has a geometry detection unit which emits a warning signal based on an alignment or non-parallelism of segment boundaries, and
wherein the evaluation device displays the warning signal as an indication of a desired alignment of the terminal device to be changed on the screen thereof.

14. The method according to claim 7,
wherein known tooth shapes occurring in practice for defining the segments and/or for improving the geometry detection are stored in the evaluation device and are compared with the detected shapes or segment boundaries.

15. The method according to claim 1,
wherein the capture device comprises an ambient light sensor, the output signal of which is fed to the evaluation device.

16. The method according to claim 1,
wherein the evaluation device, after a predetermined number of evaluations, carries out the preparatory step again, taking into account any evaluations that have been carried out.

17. The method according to claim 1,
wherein the capture device is designed as a camera and the evaluation device comprises a smartphone app, said app performing at least part of the evaluation via the evaluation device.

18. The method according to claim 1,
wherein the capture device is designed as a scanner, where said scanner integrates a computer, which performs at least part of the evaluation via the evaluation device.

19. A computer program product for a method for determining a tooth colour comprising program code which is stored on a non-transitory machine-readable medium, the machine readable medium comprising computer instructions executable by a processor, which computer instructions cause an evaluation device to perform the method according to claim 1.

20. A method for determining a tooth colour, comprising providing an evaluation device having an iterative learning algorithm using Convolutional Neural Networks (CNNs), wherein the algorithm is trained on previously known RGB tooth colours,
in a preparatory step, based on at least one previously known RGB tooth colour, acquiring images of one or more tooth colours under different lighting conditions and different capture angles, wherein the one or more tooth colours are perceived as three separate layers,
in an evaluation step, evaluating the images using the evaluation device and assigning the images of the one or more tooth colours to the applicable RGB tooth colour based on learned mapping from the known RGB tooth colour, thereby creating a learned assignment for each RGB tooth colour,
providing a capture device, which device captures an image of an auxiliary body having a previously known RGB tooth colour together with at least one tooth of undetermined colour,
acquiring, using the capture device, at least two images of the combination of the tooth with an undetermined colour and the auxiliary body from different capture angles and feeding the at least two acquired images to the evaluation device, and
evaluating, using the evaluation device, the at least two acquired images, and outputting, based on the learned assignment to each of the RGB tooth colours, a calculated tooth colour for the tooth with the undetermined colour according to a reference value, which comprises a tooth colour key.

21. The method according to claim 20,
wherein the capture device comprises a camera of a terminal device.

* * * * *